United States Patent

Shadd, Jr.

[11] Patent Number: 6,053,894
[45] Date of Patent: Apr. 25, 2000

[54] HYPODERMIC SYRINGE

[76] Inventor: Daniel L. Shadd, Jr., 546 Sandralee Dr., Toledo, Ohio 43612

[21] Appl. No.: 08/985,228

[22] Filed: Dec. 4, 1997

Related U.S. Application Data

[63] Continuation-in-part of application No. 08/905,411, Aug. 4, 1997.

[51] Int. Cl.[7] ........................................... A61M 5/00
[52] U.S. Cl. ........................ 604/191; 604/187; 604/229; 604/110
[58] Field of Search ................................ 604/218, 187, 604/227, 228, 229, 110, 191, 219

[56] References Cited

U.S. PATENT DOCUMENTS

| | | | |
|---|---|---|---|
| 2,860,639 | 11/1958 | Hoover | 606/234 |
| 3,985,122 | 10/1976 | Topham | 604/191 |
| 4,688,571 | 8/1987 | Tesler | 606/234 |
| 4,758,223 | 7/1988 | Rydell | 604/98 |
| 4,846,801 | 7/1989 | Okuda et al. | |
| 4,997,423 | 3/1991 | Okuda et al. | |
| 5,242,405 | 9/1993 | Howe | 604/125 |
| 5,458,576 | 10/1995 | Haber et al. | |
| 5,512,054 | 4/1996 | Morningstar | |
| 5,554,132 | 9/1996 | Straits et al. | |
| 5,782,803 | 7/1998 | Jentzen | 604/110 |

*Primary Examiner*—Corrine McDermott
*Assistant Examiner*—Kent Gring
*Attorney, Agent, or Firm*—Donald R. Fraser

[57] ABSTRACT

A hypodermic syringe is disclosed wherein the medicine in the outlet tube leading to the hollow needle is caused to be injected into the patient. The expulsion of the fluid medicine from the outlet tube of the syringe is accomplished by an auxiliary piston which is normally carried by a primary piston. The mechanism used to force movement of the primary piston continues to drive an auxiliary piston, after the primary piston is stopped, to effectively force fluid medicine out of the outlet tube. Thereby, the amount of fluid medicine which may be discarded will lessen considerably.

13 Claims, 3 Drawing Sheets

HYPODERMIC SYRINGE

This is a continuation-in-part application of U.S. patent application Ser. No. 08/905,411 filed Aug. 4, 1997.

FIELD OF THE INVENTION

The present invention relates to a hypodermic syringe used to inject liquid medicaments under the skin for therapeutic purposes. More particularly, the invention relates to a novel structure of a hypodermic syringe plunger capable of expelling substantially all of the liquid medicament contained in the syringe reservoir.

BACKGROUND OF THE INVENTION

Hypodermic syringes known to the prior art typically were designed to properly administer a predetermined volume of medicament. However, the design of the hypodermic syringe permitted a small quantity of the liquid medicament to remain within the zone immediately adjacent to outlet of the main reservoir and the inlet to the hollow needle.

SUMMARY OF THE INVENTION

It is an object of the present invention to produce a hypodermic syringe structure for use in the medical field for injecting liquid medicaments under the skin which structure is capable of substantially completely voiding the entire volume of the liquid medicament contained therein.

It is another object of the invention to produce a hypodermic syringe for use in the medical field which may be equipped with a fanciful exterior portion attached to the plunger or piston operating mechanism.

Still another object of the invention is to produce a hypodermic syringe for use particularly with children wherein the handle of the syringe is provided with a removal head portion to be presented to the child after being given a hypodermic injection.

It is still another object of the invention to produce a hypodermic syringe wherein at least a portion of the components are provided with pleasing colors.

The objects and advantages of the invention may be typically achieved by a hypodermic syringe comprised of a hollow cylindrical body portion one end terminating in an outlet tube of a diameter smaller than the diameter of the cylindrical body portion; a hollow hypodermic needle communicating with the outlet of the body portion; a primary piston disposed within and adapted by reciprocal movement within the cylindrical body portion; shaft means attached to the primary piston and extending outwardly of the end of the body portion; shaft means attached to the primary piston and extending outwardly of the end of the body portion opposite the outlet tube and operative to impart reciprocating movement to the primary piston toward and away from the outlet tube of the body portion; and an auxiliary piston carried by the primary piston and adapted to enter the interior of the outlet tube of the body portion after the primary piston contacts the outlet tube.

BRIEF DESCRIPTION OF THE DRAWINGS

The above, as well as other, objects and advantages of the invention will become readily manifest to those skilled in the art from reading the following detailed description of an embodiment of the invention when considered in the light of the accompanying drawings, in which.

DETAILED DESCRIPTION OF THE PREFERRED EMBODIMENT

Figure 1:
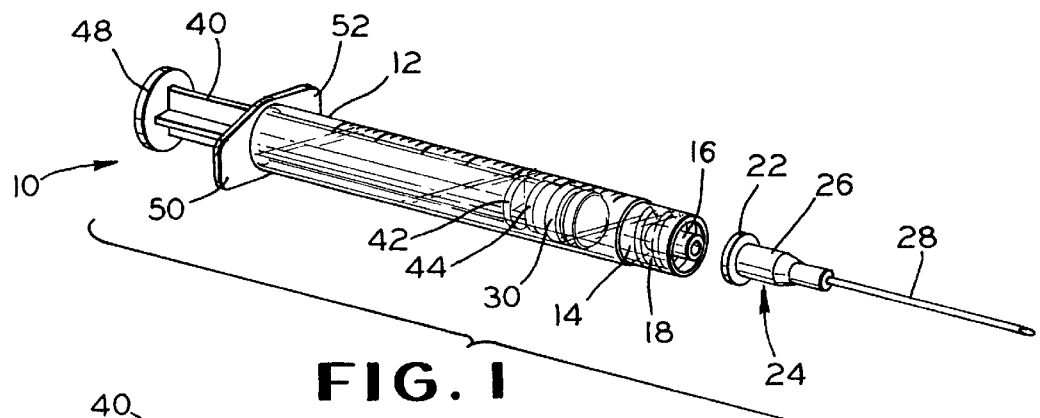
FIG. 1 is an exploded perspective view of a hypodermic syringe incorporating the features of the invention.
Figure 2:
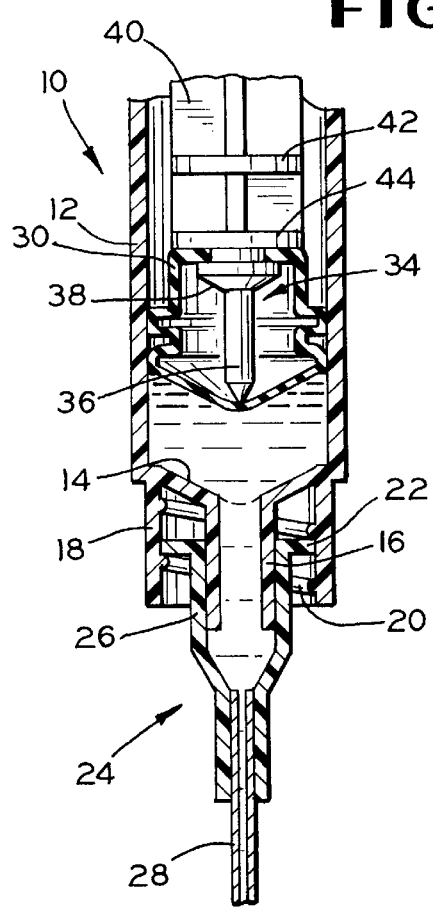
FIG. 2 is a fragmentary sectional view of the syringe illustrated in FIG. 1 showing the primary piston of the syringe approaching evacuation of the medicine in the main reservoir of the syringe.
Figure 3:
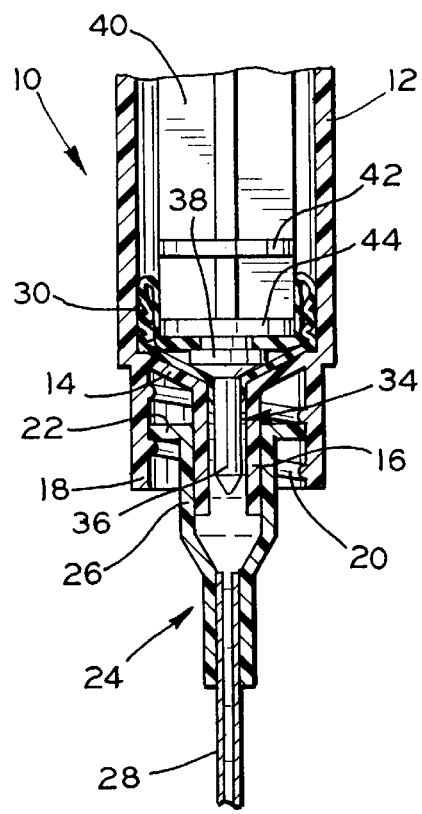
FIG. 3 is a fragmentary sectional view of the syringe similar to FIG. 2 showing the primary piston in its fully inserted position and the auxiliary piston after puncturing the primary piston and evacuating the medicine in the outlet tube.

Referring to FIGS. 1, 2, and 3, there is illustrated a hypodermic syringe embodying the features of the present invention. More specifically, there is shown a hypodermic syringe, generally indicated by reference numeral 10, which includes a hollow cylindrical body portion 12. One end of the hollow cylindrical body portion 12 is closed by an end wall 14 having an outlet tube 16. The outlet tube 16 is formed to have an inside diameter which is considerably smaller than the body portion 12 and is coaxial therewith. It will be noted that the end wall 14 is formed to be frusto-conical in shape.

A downwardly depending or outwardly extending hollow cylindrically shaped extension 18 is formed integral with the end wall 14. The interior surface of the extension 18 is provided with helically extending threads 20. The threads 20 are adapted to receive the outwardly extending annular flanged section 22 of an associated hollow hypodermic needle coupling 24. The needle coupling 24 includes a main body 26 which at the upper end terminates in the annular flange 22, while the opposite end is tapered and is adapted to snugly engage one end of a hollow hypodermic needle 28.

A hollow, generally cylindrically shaped, plunger of piston 30 is disposed for reciprocal movement within the interior of the body portion 12. The piston 30 is typically formed of an elastomeric material such as, for example, rubber. The exterior of the piston 30 is provided with radially outwardly extending ribs 32 which extend completely around the outer surface thereof. The ribs 32 are provided to create a seal between the piston 30 and the interior wall surface of the body portion 12.

An auxiliary plunger or piston 34 is disposed within the hollow interior of the piston 30. The auxiliary piston 34 includes an elongate shaft 36 one end of which is pointed and the other end is provided with laterally outwardly extending head 38.

A rod or shaft 40, having spaced apart disc-shaped guide members 42, 44 at one end, is adapted for reciprocal movement within the interior of the hollow body portion 12. The end of the shaft 40 opposite the end containing the guide members 42, 44 is provided with a radially outwardly extending annular flange 48.

The end of the hollow cylindrically body portion 12 opposite the end wall 14 is provided with oppositely extending finger grasping arms 50, 52. The arms 50, 52 cooperate with the annular flange 48 of the shaft 40 to facilitate in the operation of the syringe. More specifically, the person responsible for administering the medicine by way of a hypodermic inspection initially grasps the syringe illustrated in FIGS. 1, 2, and 3 by holding body portion 12 with the fingers of one hand and insert the end of the hollow needle 28 into the sealed container of the desired medicine and thence withdraws the piston 30 by pulling shaft 40 outwardly of the body portion 12. Such action is effected by grasping the annular flange 48 by the user's free hand. The outward movement of the piston 30 creates sufficient vacuum to cause the medicine to flow into the zone defined by the end wall 14 and the bottom wall of the piston 30. The movement is continued until the desired volume of medicine is received within the syringe reservoir. Typically, this is determined visually by observing volumetric indicia appearing on the wall of the body portion 12. This is readily accomplished since the body portion 12 is typically formed of optically transparent material such as glass or plastic.

As soon as the desired volume of fluid is received, the outward movement of the piston 30 is ceased and the needle 28 is removed from the supply thereof. The syringe 10 is now ready to be used in administering the medicine.

The end of the needle 28 is caused to be inserted under the patient's skin and the person administering the injection typically places the index and adjacent finger the underside of the arms 50, 52, respectively, while the thumb of the same hand is placed on the exposed surface of the annular flange 48. Then, the thumb and fingers are forced toward one another causing the piston rod 40 to force the piston 30 toward the outlet end 14. Simultaneously, the medicine contained within the reservoir with the cylindrical body portion 12 is forced through the outlet tube 16, the hollow needle 28, and finally into the patient.

When the piston 30 contacts the outlet end wall 14, all of the fluid within the reservoir of the hollow cylindrical body piston 12 will be expelled. However, medicine will remain in the outlet tube 16.

The medicine within the outlet tube 16 is expelled from the syringe of the invention by further axial pressure being applied to the piston rod 40 causing the end thereof to apply pressure to the head 38 of the auxiliary piston 34 causing the pointed end of the shaft 36 to puncture the elastomeric media of the primary piston 30 and allow it to proceed into the interior of the outlet tube 16 expelling the fluid medicine therefrom until the base of the head 38 contacts that portion of the primary piston 30 which is immediately over or superimposed on the upper surface of the end wall 14. In such fashion, the medicine within the outlet tube 16 which would otherwise have been discarded along with the syringe, would be injected into the patient. Manifestly the syringe calibration would necessarily be calibrated to reflect the additional useful volume of fluid medicine to be injected.

Since injections are oftentimes associated with unpleasant thoughts, particularly in the minds of children, the present invention contemplates the use of pleasant colors in the fabrication of the syringe and its various components. In particular, the glass or plastic used to fabricate the hollow cylindrical body portion 12 should carry eight absorbing dyes or pigments to effect the desired color.

Figure 4:
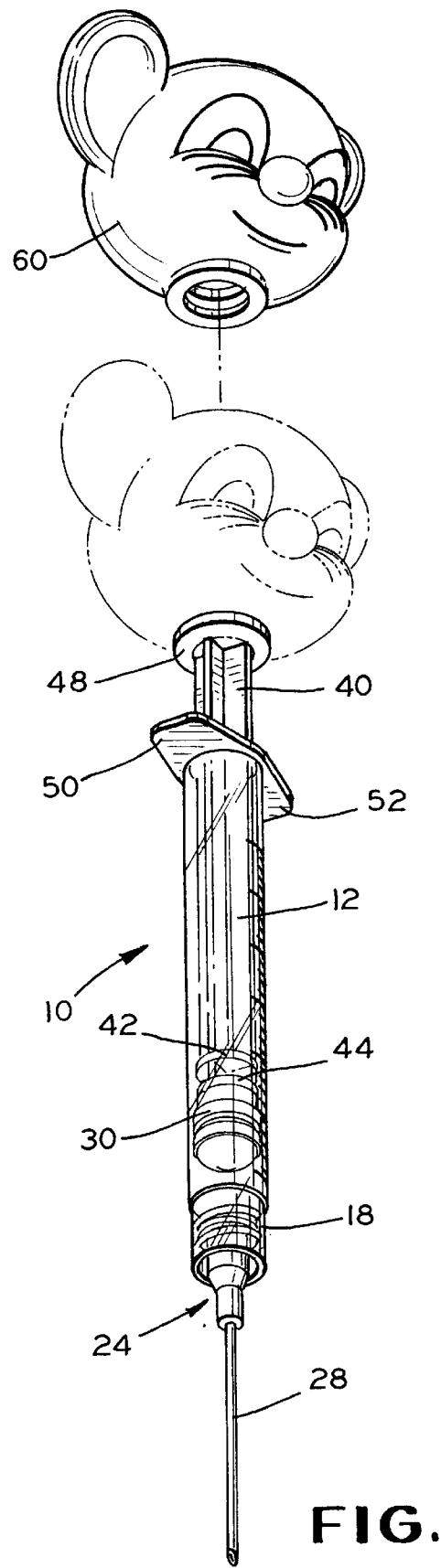
FIG. 4 is an exploded perspective view of the hypodermic syringe structure illustrated in FIGS. 1, 2, and 3 illustrating a removable head of a fanciful design.

FIG. 4 discloses still another embodiment of the invention wherein a fanciful head 60 formed of an elastomeric material which may be placed on the outermost end 48 of the piston rod 40. The head 60 may be any of the contemporary figures known to children and can be readily removably mounted. The removably mounted head 60 may be removed from the syringe after the injection and awarded to the child, for example, as a token of bravery.

Figure 5:
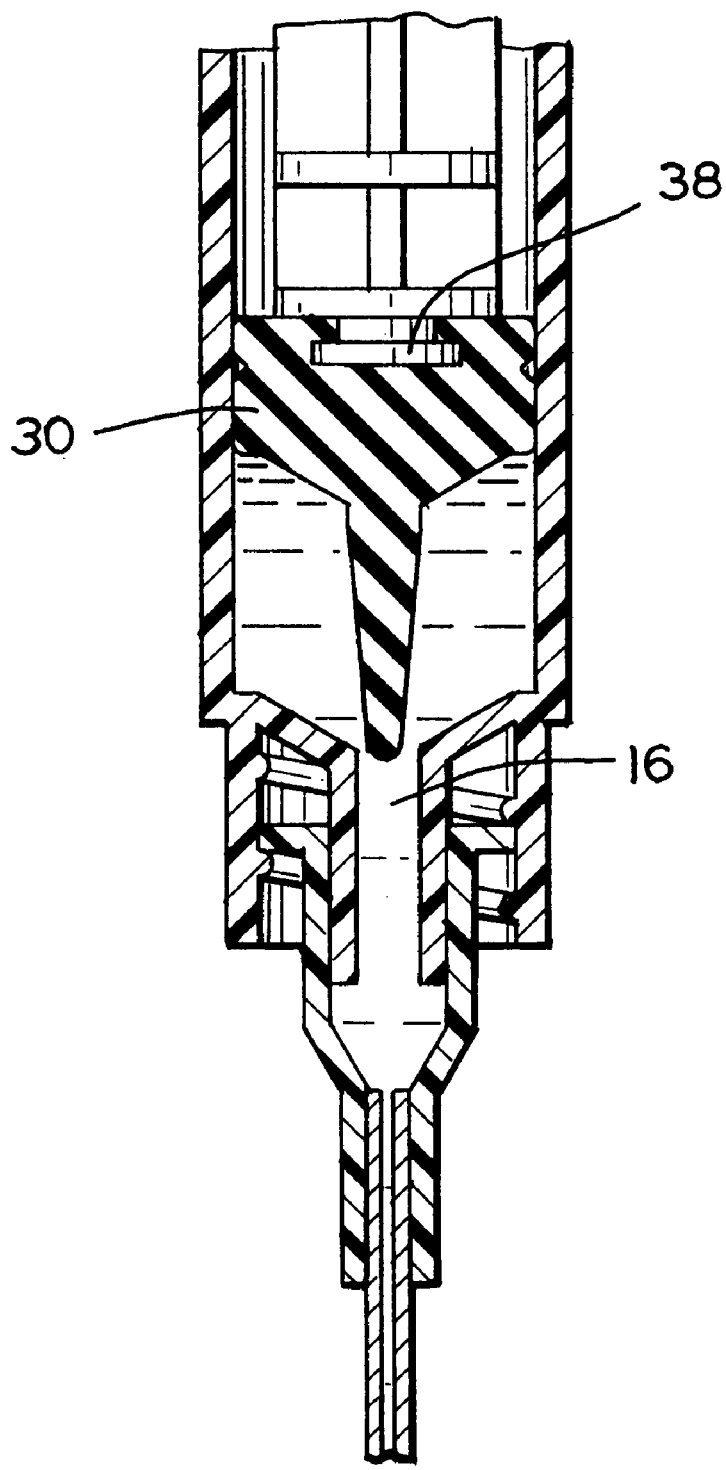
FIG. 5 is a fragmentary sectional view of an embodiment of a syringe similar to that illustrated in FIGS. 1, 2, and 3 showing an alternative auxiliary portion just prior to being inserted into the outlet tube.

FIG. 5 discloses another embodiment of the invention wherein the basic syringe structure is utilized and prime reference numerals are used to identify similar structural elements. More specifically, an auxiliary piston 70 having an elongate tapered nose 72 is attached to the laterally extending head 74 spaced inwardly from and integral with the innermost of the quick members 42', 44' of the shaft 40'. The end of the piston 70 opposite the tapered nose 72 is provided with a recessed cavity 76 having a radially inwardly extending lip 78. The head 74 is received within the recessed cavity 76 and the lip 78 functions to retain and the head 72. The structure provides an attachment between the shaft 40' and the auxiliary piston 70 permitting simultaneous movement of the piston 70 upon reciprocal movement of the shaft 40' with respect to the associated hollow cylindrical body portion 12' of the syringe 10'.

The taper of the nose 72 is such that when the auxiliary piston 70 is driven downwardly, the nose 72 fits perfectly into the outlet tube 16' thereby completely evacuating the medicament with the zone defined by the tapered outer wall of the auxiliary piston 70 and the interior of the cylindrical body 12' and the associated outlet tube 16'.

In accordance with the provisions of the patent statutes, the present invention has been described in what is considered to represent its preferred embodiment. However, it should be understood that the invention can be practiced otherwise than as specifically illustrated and described without departing from its spirit or scope.

What is claimed is:

1. A hypodermic syringe comprised of:
    a) a hollow cylindrical body portion, one end terminating in an outlet tube of a diameter smaller than the diameter of the cylindrical body portion;
    b) a hollow hypodermic needle communicating with the outlet tube of said body portion;
    c) a primary piston comprising an elastomeric material disposed within and adapted for reciprocal movement within said cylindrical body;
    d) shaft means attached to said primary piston and extending outwardly of the end of said body portion opposite the outlet tube and operative to impart reciprocating movement to said primary piston to ward and away from the outlet tube of said body portion; and
    e) an auxiliary piston carried by and positioned within said primary piston, said auxiliary piston adapted to puncture the elastomeric material of said primary piston and enter the interior of the outlet tube of said body portion after said primary piston contacts the outlet tube.

2. A hypodermic syringe as defined in claim 1 wherein said shaft means includes a first end affixed to said primary piston and a second end extending outwardly of said cylindrical body portion.

3. A hypodermic syringe as defined in claim 2 including a fanciful thumb engaging portion affixed to the second end of said shaft.

4. A hypodermic syringe as defined in claim 3 wherein said thumb engaging portion is removably affixed to the second end of said shaft.

5. A hypodermic syringe as defined in claim 1 wherein at least said hollow cylindrical body is formed of a colored material.

6. A hypodermic syringe as defined in claim 1 wherein said hollow cylindrical body is formed of optically transparent material.

7. A hypodermic syringe as defined in claim 6 wherein said transparent material contains a color emitting substance.

8. A hypodermic syringe as defined in claim 2 wherein said auxiliary piston includes an elongate piston shaft receivable within the outlet tube of said body portion.

9. A hypodermic syringe as defined in claim 8 wherein the elongate piston shaft is capable of extending outwardly of said primary piston and receivable within the interior of the outlet tube of said body portion.

10. A hypodermic syringe as defined in claim 1 wherein said auxiliary piston is formed of an elastomeric material.

11. A hypodermic syringe as defined in claim 10 wherein said auxiliary piston includes an elongate end portion adapted to be snugly received within the outlet tube.

12. A hypodermic syringe as defined in claim 11 wherein the elongate end portion of said auxiliary piston is tapered.

13. A hypodermic syringe as defined in claim 1 wherein said auxiliary piston is provided with a recessed cavity and associated lip portion for receiving said shaft means.

* * * * *